US008035088B2

(12) United States Patent
Tomany et al.

(10) Patent No.: US 8,035,088 B2
(45) Date of Patent: Oct. 11, 2011

(54) DEVICE, APPARATUS AND METHODS FOR MASS SPECTROMETRY

(75) Inventors: Michael J. Tomany, Thompson, CT (US); Joseph A. Jarrell, Newton Highlands, MA (US); Stanislaw Koziol, Wrentham, MA (US); Wade P. Leveille, Douglas, MA (US)

(73) Assignee: Waters Technologies Corporation, Milford, MA (US)

( * ) Notice: Subject to any disclaimer, the term of this patent is extended or adjusted under 35 U.S.C. 154(b) by 73 days.

(21) Appl. No.: 12/593,313

(22) PCT Filed: Mar. 19, 2008

(86) PCT No.: PCT/US2008/057505
§ 371 (c)(1),
(2), (4) Date: Feb. 11, 2010

(87) PCT Pub. No.: WO2008/124264
PCT Pub. Date: Oct. 16, 2008

(65) Prior Publication Data
US 2010/0133431 A1     Jun. 3, 2010

Related U.S. Application Data

(60) Provisional application No. 60/910,490, filed on Apr. 6, 2007.

(51) Int. Cl.
*H01J 49/04* (2006.01)
*H01J 49/26* (2006.01)
*B01D 59/44* (2006.01)
(52) U.S. Cl. ........ 250/428; 250/434; 250/435; 250/281; 250/282; 250/288; 250/287; 137/561 A
(58) Field of Classification Search .................. 250/428, 250/434, 435, 281, 282, 288, 287; 137/561 A
See application file for complete search history.

(56) References Cited

U.S. PATENT DOCUMENTS

| | | | |
|---|---|---|---|
| 5,917,184 A * | 6/1999 | Carson et al. ................ 250/288 |
| 6,462,336 B1 | 10/2002 | Bajic |
| 6,974,957 B2 * | 12/2005 | Glukhoy ...................... 250/427 |
| 7,071,466 B2 | 7/2006 | Glukhoy |
| 7,148,472 B2 * | 12/2006 | Glukhoy ...................... 250/287 |
| 2003/0020011 A1 | 1/2003 | Anderson et al. |
| 2004/0232052 A1 | 11/2004 | Call et al. |
| 2010/0148057 A1 * | 6/2010 | Jarrell et al. ................ 250/282 |

* cited by examiner

*Primary Examiner* — Nikita Wells

(57) ABSTRACT

The invention comprises apparatus for use with atmospheric pressure ionization sources in which an aerosol is formed from a solution of a sample. The aerosol is received in a hollow member and discharged outside the chamber of the ionization source in order to reduce contamination of the ionization source itself by involatile material in the solution and by previously analysed samples. The hollow member is easily removable from the ionization source to facilitate cleaning and replacement. Ionization sources, mass spectrometers, and ion mobility spectrometers comprising the apparatus are also described.

29 Claims, 6 Drawing Sheets

DEVICE, APPARATUS AND METHODS FOR MASS SPECTROMETRY

CROSS REFERENCE TO RELATED APPLICATIONS

This application is the National Stage of International Application No. PCT/US2008/057505, filed Mar. 19, 2008, which claims priority to and benefit of U.S. Provisional Patent Application Ser. No. 60/910,490 filed Apr. 6, 2007. The entire contents of these applications are incorporated herein by reference.

FIELD OF THE INVENTION

This invention relates to apparatus for use with ion sources commonly associated with mass spectrometers and ion mobility spectrometers.

STATEMENT REGARDING FEDERAL SPONSORSHIP

No Federal or State money was used to develop the present invention.

BACKGROUND OF THE INVENTION

Mass spectrometers are used to identify and quantitate compounds. Mass spectrometers analyse compounds by the mass to charge ratio of ions formed of the molecules of such compounds or the fragments of such molecules. Mass spectrometers generally have ion sources, which provide ions of the compounds for analysis. One form of ion source is an atmospheric pressure ionization (API) sources. An API source is, as its name suggests, an ion source that creates ions at approximately atmospheric pressure. These ions are directed to substantially closed sections of the mass spectrometer operating at low pressure or vacuum.

API sources suitable for generating ions from solutions include electrospray, atmospheric pressure chemical ionization (APCI) and atmospheric pressure photoionization (APPI) sources, all of which involve the formation of an aerosol from the solution. Electrospray sources form the aerosol by means of an electrical field created between an inlet capillary through which the solution is introduced and a counter electrode disposed downstream of the exit of the capillary. This electrical field also results in the ionization of at least some of a sample dissolved in the solution. APCI and APPI ion sources form the aerosol by means of a nebulizer, usually a concentric flow pneumatic nebulizer, and further comprise additional means for ionizing sample molecules comprised in the aerosol. These additional means may comprise a corona discharge (APCI sources) or a beam of photons (APPI sources). A nebulizer may also be used in electrospray sources to increase the maximum solution flow rate that the source can accept. Ionization may also be effected by a combination of some or all of the methods described.

API sources, which produce an aerosol comprising electrically charged droplets of the solution, are produced in a region containing gas at approximately atmospheric pressure. The charged droplets may comprise solvated ions characteristic of the sample dissolved in the solution. Droplets and solvated ions are sampled from the aerosol into a region of lower pressure through a small orifice or capillary tube, usually along a sampling axis inclined to the central axis of the aerosol. At least some of the ions entering the region of lower pressure are subsequently transmitted to a mass analyser through a sequence of vacuum chambers of progressively reducing pressure. These vacuum chambers usually comprise ion guides of various types. Mass analysers used in conjunction with these ion sources include linear quadrupoles, quadrupole, cylindrical and "Kingdon" ion trap analysers, magnetic sector analysers, ion cyclotron resonance analysers (ICR or FTMS analysers), time-of-flight analysers, or combinations of these analysers for use in tandem (MS/MS) apparatus. API ion sources are also used in ion mobility spectrometers, including field asymmetric ion mobility spectrometers (FAIMS) and in mass spectrometers comprising an ion mobility stage as well as more conventional mass filters or analysers. The charged droplets present in the aerosol may be at least partly desolvated through contact with gas molecules present in the atmospheric pressure region of the source. Desolvation may also be assisted by suitably directing (relative to the aerosol axis) gas flows into that region, and/or by heating the capillary, nebulizer and gas flows. Improved desolvation may also be obtained by heating the wall enclosing the atmospheric pressure region, particularly in the vicinity of the orifice through which ions may pass leave the source and pass into the mass analyser. Some prior sources also comprise means for flowing heated gas counter to the direction of travel of ions and droplets through the orifice.

Often, the solution admitted into API ionization sources is the eluent from a liquid chromatograph. Commonly used chromatographic flow rates are between 0.1 and 1.0 ml/min, but only a small fraction of the aerosol generated from the solution passes through the orifice into the region of lower pressure. The remainder of the aerosol is waste. Because the solvents (and samples) used for liquid chromatography may be poisonous, the atmospheric pressure region of an API source is usually enclosed. The chamber also serves to reduce contamination from material that may be present in the laboratory air causing interference to an analysis. As one or more flows of desolvation gas are introduced into the chamber, it must be fitted with an exhaust port through which gas and waste solvent can leave and be conducted to a safe discharge point.

Unfortunately, the majority of samples typically analysed with liquid chromatography are non-volatile, and the solvents employed often comprise non-volatile buffer salts. Because the majority of the spray does not enter the orifice, these non-volatile constituents tend to accumulate on surfaces within the atmospheric pressure enclosures, from which they may subsequently be released by contact with the aerosol to interfere with a subsequent analysis. They may also form insulating layers on electrically conducting surfaces within the chamber, which may become electrically charged and adversely affect the transport of ions into the orifice. In order to maintain performance, therefore, the atmospheric pressure chamber of prior API sources requires regular cleaning.

It is an object of the invention to provide API ionization sources and spectrometers, and apparatus for use in such ionization sources and spectrometers, in which the deposition of material on critical surfaces inside the sources is less than in prior sources. It is another object of the invention to provide API ionization sources, spectrometers and apparatus for use in such ionization sources and spectrometers that are more easily cleaned than are prior equipment. A further object of the invention is to provide apparatus for exhausting API ionization sources and spectrometers.

As used herein, "atmospheric pressure" includes the operation of an ion source in the presence of significant quantities of gas, perhaps with pressures several hundred torr either side of atmospheric pressure itself. The term is generally used in the art to distinguish this type of ionization source from those that operate under high or medium vacuum, for example, electron impact or chemical ionization sources. Further, the term "charged particles" is meant to include singly- and multiply-charged ions, solvated ions, adduct ions, and cluster ions, etc, all formed from a sample in an ionization source operating at atmospheric pressure (as defined above), and also charged droplets of solvent comprising molecules or ions characteristic of a sample.

SUMMARY OF THE INVENTION

Embodiments of the present invention are directed to apparatus, device and methods of performing mass spectrometry in which the deposition of material on critical surfaces inside the sources is readily removed. One embodiment is directed to a device for placement in a chamber of an interface housing. The interface housing has at least one wall defining the chamber and has at least one exit port and at least one working port in the wall. The chamber is for receiving an aerosol, having at least a working portion, an exiting portion and a falling or fallen portion. The working portion of the aerosol is received by the working port. The exiting portion of the aerosol flows past the working port and is received by the exit port. The fallen or falling portion of the aerosol refers to that portion not received by the exit port or the working port and falls out of suspension.

The device comprises a deflector and a support member. The deflector has aerosol deflecting surfaces and a first position in which the deflector is positioned for directing an aerosol flowing past the working port to the exit port and a second position in which the deflector is removed from the chamber. The support member is affixed to the deflector and has mounting means for removably mounting the deflector in the first position. In the second position the support member and the deflector are removed from the chamber to allow removal of the fallen portion of aerosol deposited on the device or disposal of the device.

Thus, the user's contact with substances, solvents and materials, that can be harmful, and potentially toxic, is minimized. The device can be discarded as a disposable item or more readily cleaned of the falling portion of the aerosol by immersion in cleaning solutions rather than manual wiping and blotting of the chamber wall.

Preferably, the support member has at least one planar section having a top surface, a bottom surface and at least one edge surface. At least one of the edge surface and bottom surface is removably mounted to the at least one wall with the deflector in the first position. In the first position, the top surface collects fallen aerosol, and, in said second position, the support member is removed from the chamber to allow removal of fallen aerosol deposited on the top surface.

The deflector is a foil positioned to deflect gas and aerosol in a predetermined direction. A preferred foil is a tubular member having a passage. The passage has a passage inlet and a passage outlet. The passage outlet is in fluid communication with the exit port and the passage inlet receives the exiting portion of the aerosol as the deflector assumes the first position. The tubular member may have any number of cross sectional shapes or forms such as a circle, ellipse, oval, and multisided forms.

One preferred embodiment features a deflector movably affixed to the support member to allow the deflector to be assume at least two orientations within the chamber. Thus, the deflector can be optimized for particular applications or chambers.

A preferred chamber has a bottom and the planar section of the support member, in said first position, is adjacent the bottom to collect fallen aerosol. Preferably, at least one edge of the device has a containment ridge to collect fallen aerosol.

One preferred device further comprises handle means affixed to at least one of said deflector and support member to facilitate manually grasping the device for removal or positioning in the chamber. The handle may take several forms including by way of example without limitation, tabs or knobs projecting from the top surface of the support member, tethers, and other means for gripping the device.

Preferably, the device acts as a manifold, directing the flow of gases circulating in the chamber. For example, one embodiment of the present invention features a tubular member having an opening or projections to allow working aerosol to enter the working port.

The device is preferably retained in the first position by gravity or the support member engages the wall of the chamber when the device is in the first position. One embodiment of the present invention features a bottom surface of the planar member having a adhesive for sticking to the wall of the chamber or the chamber is equipped with clips or slots for receiving the support member.

Embodiments of the present invention further comprise an apparatus in which the device, as a manifold, is part of the larger surrounding structure of the interface housing, in which it is received. The interface housing has at least one wall defining a chamber and having at least one exit port and at least one working port in the wall. The chamber receives an aerosol having at least a working portion, an exiting portion and a falling portion. The working portion is received by the working ports. The exiting portion flows past at least one working port and is received by at least one exit port. The falling portion comprises the part of the aerosol that falls out of suspension.

The device further comprises at least one manifold. The at least one manifold has a deflector and a support member, as previously described. The support member is affixed to the deflector and has mounting means for removably mounting the deflector in the first position and in the second position said support member and said deflector removed from the chamber to allow removal of the falling portion of aerosol deposited on the manifold and cleaning of the manifold or disposal of the manifold.

One embodiment of the invention features an interface housing constructed and arranged to receive sequentially a plurality of manifold devices. The plurality of manifolds may address special operating needs or be of a disposable nature to avoid the step of cleaning. Disposable manifolds are preferably made of inexpensive plastic or fiber board or a combination thereof.

Preferably, the apparatus further comprises an ionization source selected from the group consisting of photoionization means, chemical ionization means and electrospray ionization means. Embodiments of the present invention allow the chamber to receive a manifold device for each of the selected group or combinations.

The apparatus of the present invention further comprises at least one of the components of a mass spectrometer in communication with the working port. These components are selected from the group consisting of linear quadrupole mass filters, quadrupole, cylindrical or linear ion traps, magnetic sector mass analysers, "Kingdon" trap mass analysers, ICR or Fourier Transform mass analysers, and time of flight mass analysers. The invention may also comprise an ion mobility spectrometer or field-asymmetric ion mobility spectrometer (FAIMS), having an ionization source as described, or a mass spectrometer comprising both an ion mobility spectrometer and at least one mass analyser as listed above.

A further embodiment of the present invention features a method of servicing an interface housing. The interface housing has at least one wall defining a chamber and having at least one exit port and at least one working port in the wall. The chamber receives an aerosol having at least a working portion, an exiting portion and a falling portion. The working portion is received by the working port. The exiting portion flows past the working port and is received by the exit port. And, the falling portion comprises a part of said aerosol that falls out of suspension. The interface housing further has a door means, for accessing the chamber, having an open position and a closed position. The method comprising the step of placing the door means in an open position and removing, if present a manifold, and inserting a manifold having a deflector and a support member. The deflector has aerosol deflecting surfaces and, in a first position, the deflector is positioned for directing an aerosol flowing past the working port to the exit port. In a second position, the deflector is removed from the chamber. The support member is affixed to the deflector and has mounting means for removably mounting the deflector in the first position. In the second position, the support member and the deflector are removed from the chamber to allow removal of said fallen portion of aerosol deposited on the manifold or discarded. And, the method comprises the step of removably mounting the now cleaned support member with the deflector or a new support member and deflector in the first position.

These and other features and advantages will be apparent to those skilled in the art upon viewing the Figures and reading the detailed description that follows.

BRIEF DESCRIPTION OF THE FIGURES

Embodiments of the invention will now be described in greater detail with reference to the figures, in which.

DETAILED DESCRIPTION OF EMBODIMENTS OF THE INVENTION

The present invention will be described in detail with respect to preferred embodiments directed to a device in the form of a manifold for removing the falling portion of a aerosol in an interface housing for a mass spectrometer. Those skilled in the art will recognize that the present invention is capable of being modified and altered and has utility in other applications as well.

Figure 1:
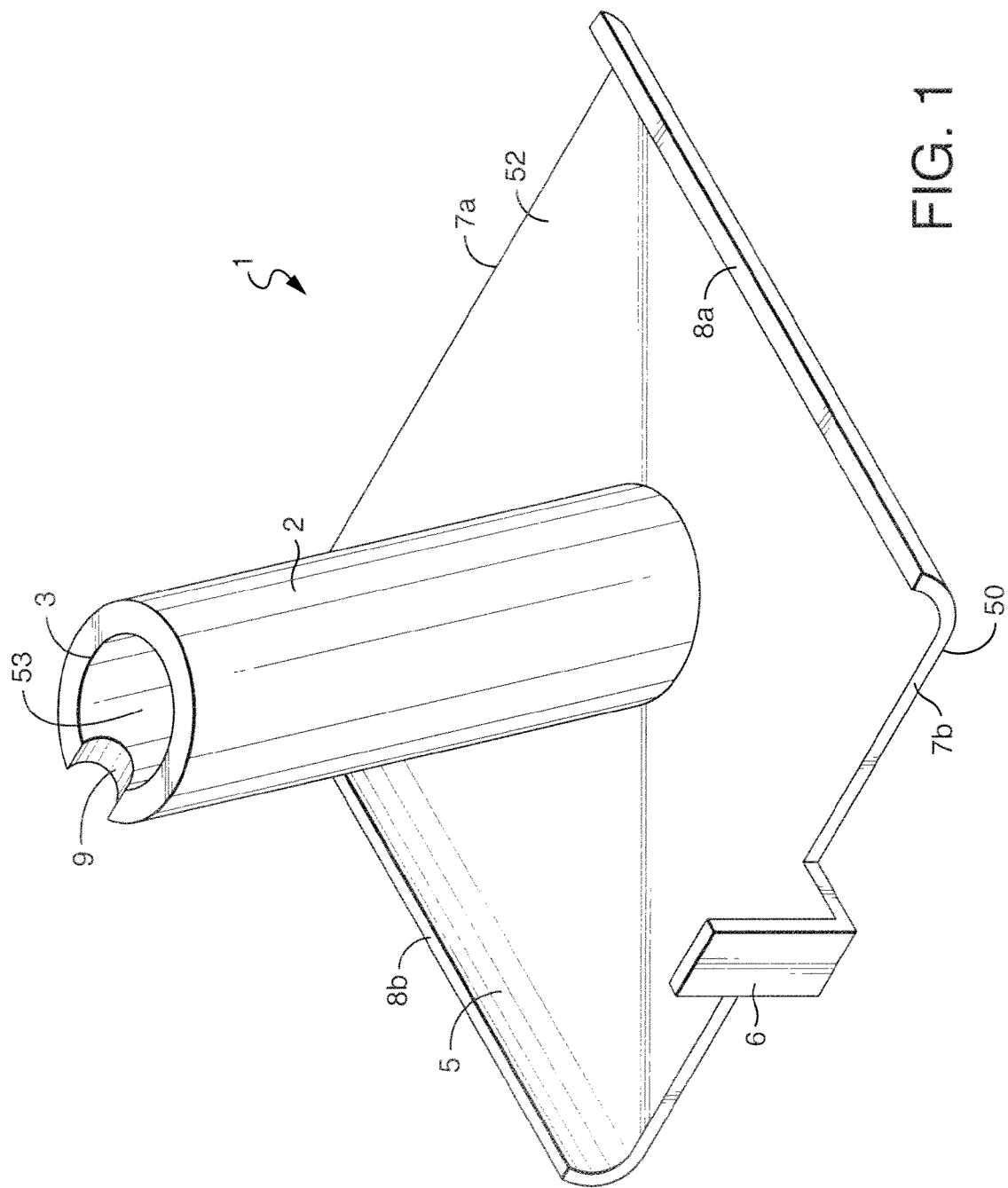
FIG. 1 is a drawing of an embodiment of apparatus for receiving an aerosol according to the invention.

Referring first to FIG. 1, a device, generally designated by the numeral 1, embodying features of the present invention is depicted. The device 1, in the nature of a manifold will be referred to in this detailed description as a device or manifold 1. The device 1 has two major elements; a support member 5 and a deflector 2. The device can be made of any rigid or semi-rigid plastic, metal, fibreboard or combinations thereof.

Figure 2:
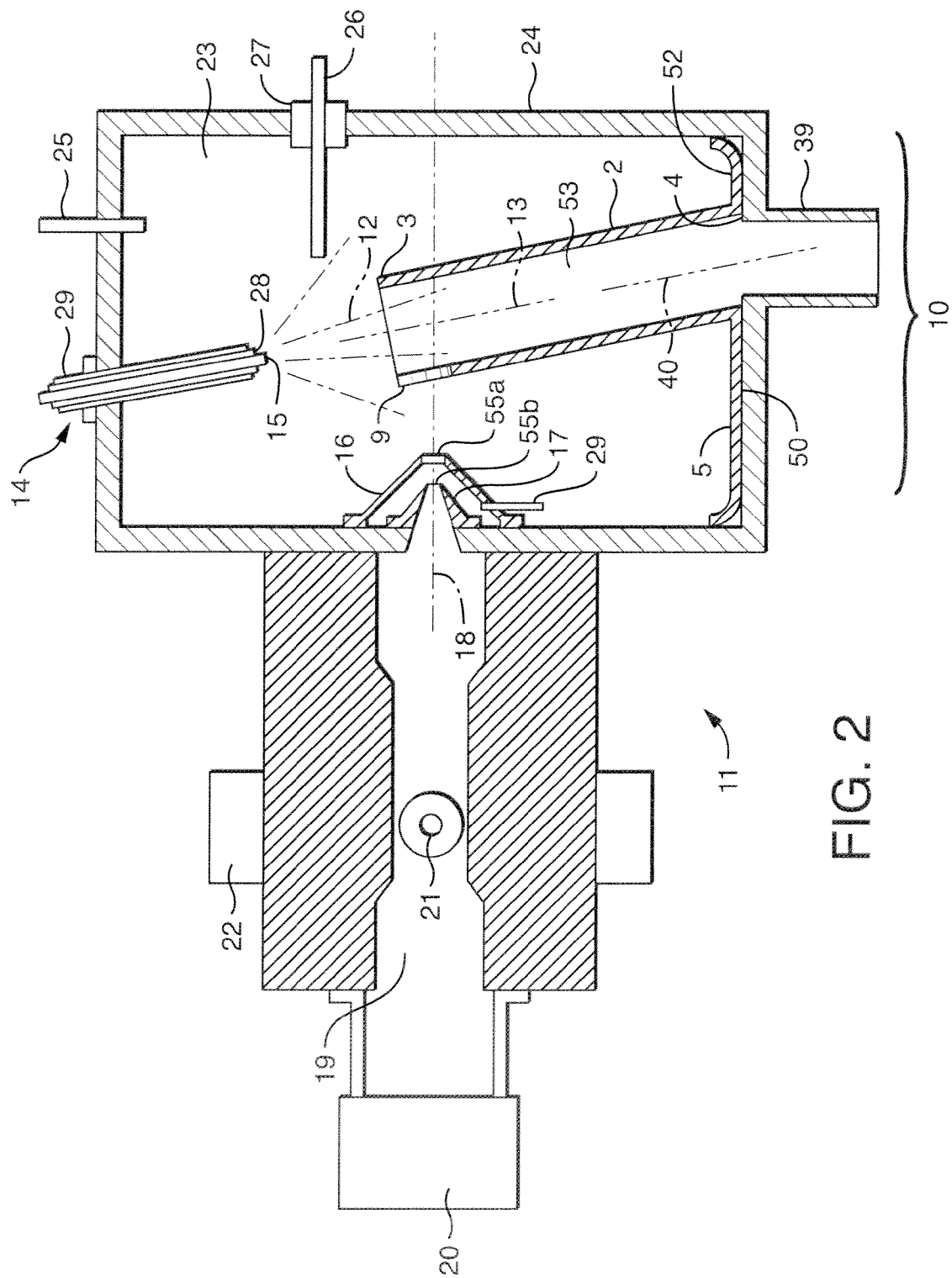
FIG. 2 is a drawing of a mass spectrometer and ionization source according to the invention.

The deflector 2 is an air foil for directing at least some of an aerosol circulating in a interface housing towards an exit port as will be described later. The deflector 2 may comprise one or more surfaces, curved or planar, for directing the flow of gases. As depicted, deflector 2 is cylindrical in shape defining a passage 53 having an entrance 3 and an exit 4, as best seen in FIG. 2. This description will refer to the deflector and the cylindrical member with the same reference number 2.

Returning now to FIG. 1, deflector 2 is affixed to support member 5 or is molded with support member 5 as a single unitary structure. The entrance 3 of the hollow member 2 comprises a cut-away portion 9, the purpose of which is described below. One embodiment of the present invention features a deflector 2 having adjustment means [not shown] in the form of being rotatably affixed to the support member 5, or having flexing joints along its length in a manner known in the art to allow the deflector 2 position and the cut-away portion 9 position to be optimized. Cutaway portion 9 may also comprise an opening [not shown] in the cylindrical member 2.

Support member 5 is generally planar and has a bottom surface 50, a top surface 52 and a first edges 7a and 7b and second edges 8a and 8b. Second edges 8a and 8b of the plate member 5 are curved as shown to facilitate positioning of support member 5 in an ionization source (as described below) and collecting falling aerosol. A lug or tab 6 projects upward from the top surface 52 to provide a gripping surface or handle for the device 1. In addition or in the alternative, lug or tab 6 may comprise a tether or knob [not shown] to facilitate handling or removal of the device 2 from an interface housing.

FIG. 2 depicts a mass spectrometer, generally designated by the numeral 11. The mass spectrometer has an interface housing, in the form of an atmospheric pressure ionization source 10, having a chamber 23 in which device 1 has been placed in a first position. An aerosol 12 is generated by a nebulizer 14 from a solution of a sample admitted into a capillary tube 15, so that droplets travel along an aerosol axis 13. A sampling housing 16 and an inlet housing 17 (in this embodiment, both hollow cones) each comprise at least one working port 55a and 55b, such as orifices in their apex, leading into an evacuated chamber 19. Gas flows from the atmospheric pressure region of the source through the working ports 55a and 55b in the housings 16 and 17. The orifice in housing 17 is smaller that that in housing 16 and serves to restrict the flow of gas to allow the pressure in the evacuated chamber 19 to be maintained between 1 and 10 torr by a mechanical vacuum pump 20. At least some charged particles pass from the aerosol 12 along a sampling axis 18, through the working ports 55a and 55b in housings 16 and 17, and subsequently through a third orifice 21 into a mass analyser 22, as discussed in more detail below.

The aerosol 12 is generated inside interface housing 10 having a chamber 23 bounded by a wall 24. Chamber 23 typically contains an inert gas (eg, nitrogen) at atmospheric pressure (as defined above), which may be introduced though a gas inlet 25. In the case of an electrospray ionization source, sample solution introduced into a capillary tube 15 may be sprayed into the chamber 23 by maintaining an electrical potential difference between the capillary 15 and the sampling housing 16 an/or a counter electrode (not shown), thereby generating the aerosol 12. This well-known electrospray process produces charged particles and/or droplets in the aerosol that may comprise ions characteristic of the sample. At least some of these charged particles then pass along the sampling axis 18 and are mass analysed, as described.

Figure 3:
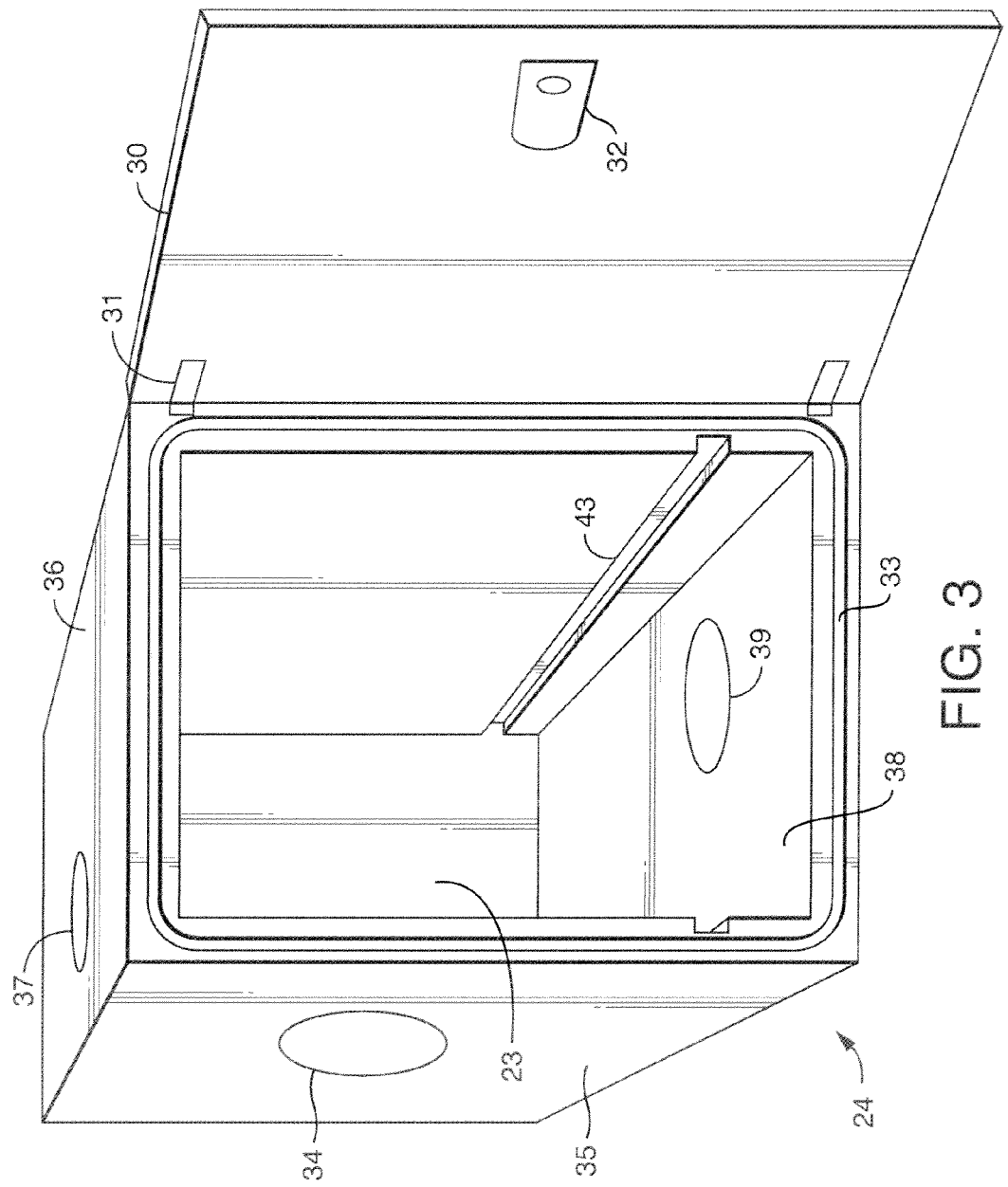
FIG. 3 is more detailed drawing of part of the ionization source shown in FIG. 2.
Figure 4:
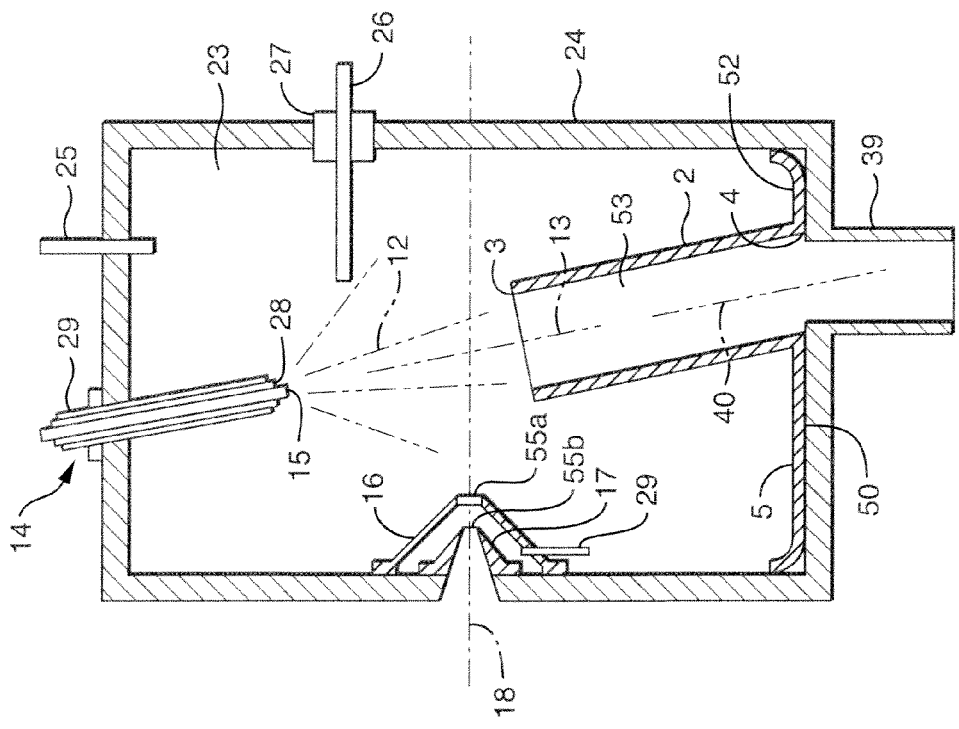
FIG. 4 is drawing of part of an ion source according to the invention having a first embodiment of a hollow member.
Figure 5:
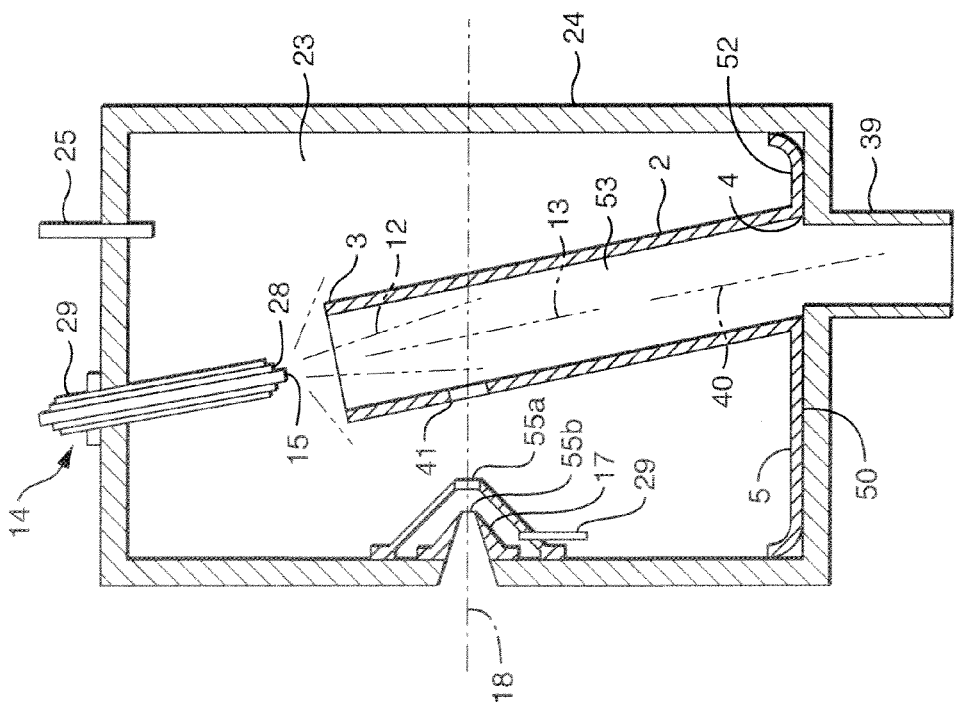
FIG. 5 is a drawing of part of an ion source according to the invention having a second embodiment of a hollow a member.
Figure 6:
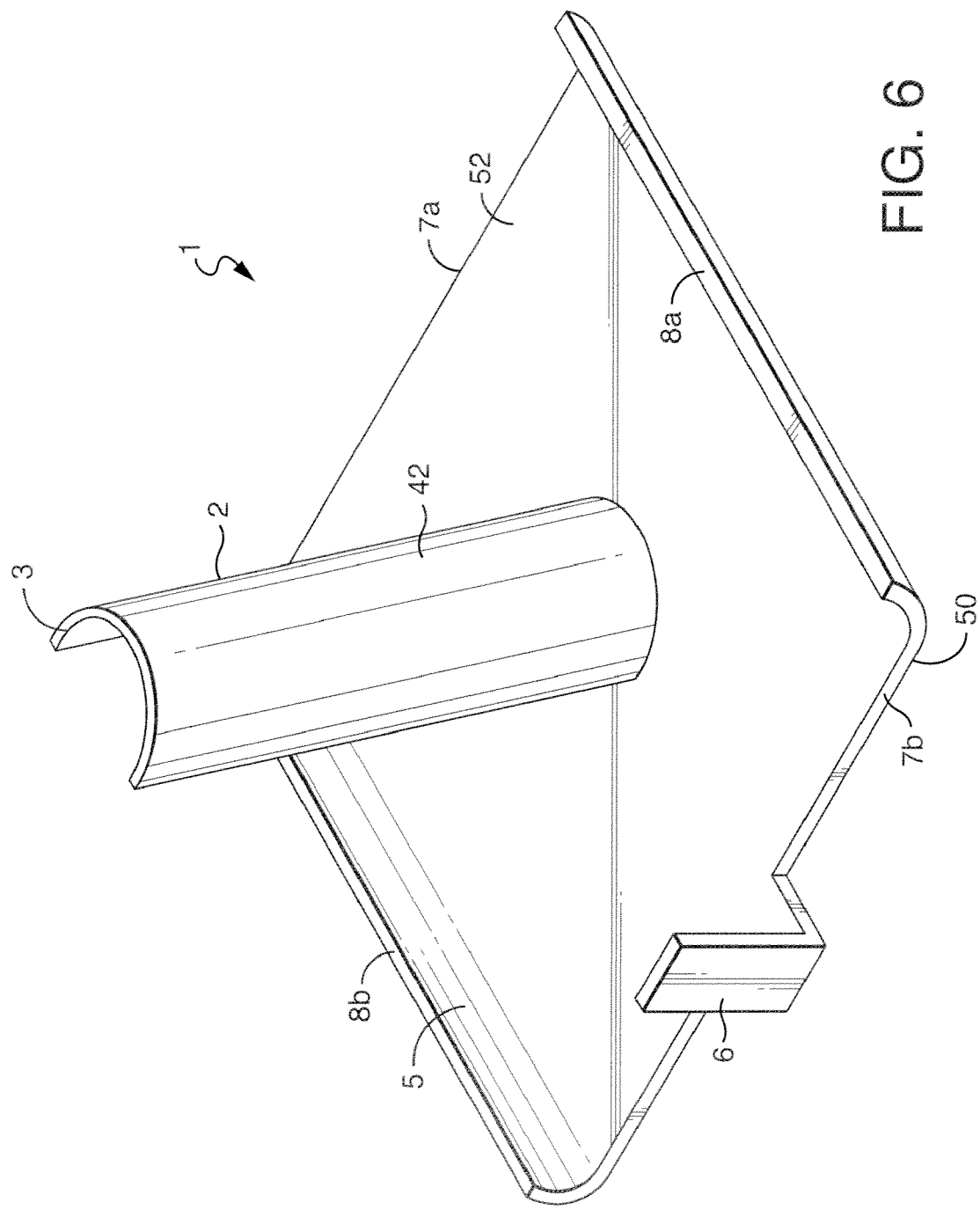
FIG. 6 is a drawing of part of an ion source according to the invention having a third embodiment of a hollow member according to the invention.
Figure 7:
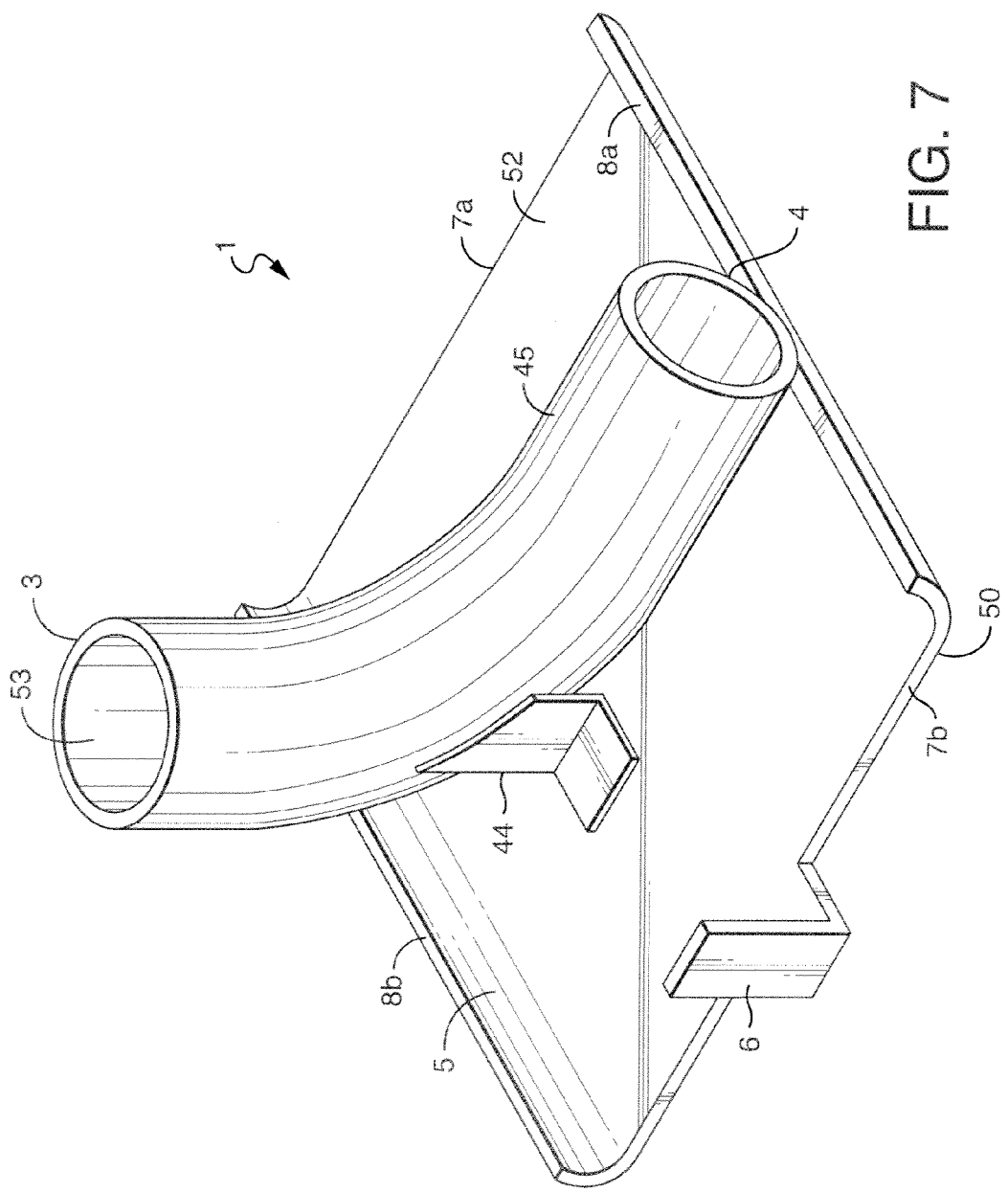
FIG. 7 is a drawing of an alternative apparatus according to the invention.

In the case of an atmospheric pressure chemical ionization (APCI) source, charged particles may be produced from the aerosol by a corona discharge generated by application of a suitable potential difference between the wall 24 and a corona electrode 26 supported in an insulator 27 in the wall 24. In such a source the aerosol 12 is generated by a nebulizer 14 that may be a concentric flow pneumatic nebulizer in which a nebulizing gas (e.g., nitrogen) is introduced through a tube 28 surrounding and concentric with the capillary 15. Such a nebulizer also may be advantageously employed in electrospray ion sources to increase the maximum solution flow rate that the source can accept. Preferably the nebulizing gas and the components of the nebulizer 14 are heated.

Atmospheric pressure photoionization (APPI) sources and spectrometers according to the invention may comprise apparatus as shown in FIG. 2 having a nebulizer 14, but in which the corona electrode 26 is omitted. Instead, ionization is instead effected by a beam of photons from a UV lamp or laser (not shown), which is directed to impinge on the aerosol.

In order to assist desolvation of the charged particles entering the sampling housing 16, both the sampling housing and the inlet housing 17 may be heated. A heated desolvation gas (sometimes known as a "cone gas") may also be introduced from the gas inlet 29 into the space between the housings so that it flows out of the orifice in the apex of the sampling housing 16 into the enclosure 23. As in conventional ionization sources, both housings 16 and 17 may comprise hollow cones with the orifices formed in their apices. Desolvation of the aerosol may be assisted by a flow of gas introduced through one or more inlets 25 and 29 (inlet 29 surrounds the capillary tube 15 and nebulizing gas inlet 28).

Referring next to FIG. 3, the wall 24 of the chamber 23 may comprise a closed box-like structure having an access door 30 attached by hinges 31 to the wall 24. Access door 30 is secured when closed by a handle catch 32. A seal 33 fitted in a recess in the wall 24 may seal the chamber 23 when the door 30 is closed. Those skilled in the art will recognize that door 30 may be secured to the wall 24 by any means which allow the door 30 to be removed. By way of example, without limitation, door 30 can be secured with screws and bolts, clips, clamps and pins.

Wall 24 comprises an aperture 34 that receives the sampling housing 16 and inlet housing 17. When assembled in a mass spectrometer the housing of the evacuated chamber 19 abuts the face 35 of the wall 24. Face 36 of wall 24 comprises another aperture 37 to which an assembly comprising the nebulizer 14 and inlet capillary 15 are fitted.

In use, in order to receive at least some of the aerosol 12, the device 1 of FIG. 1 is disposed inside the chamber 23, as shown in FIG. 2. To allow the device 1 to be easily removed for cleaning or replacement, the plate member 5 may rest on the lower face 38 of the wall 24 with the edges 7*a* and 7*b* and 8*a* and 8*b* in contact with the vertical portions of wall 24, as shown in FIG. 2. This ensures proper location of the device, which is maintained in position in the chamber 23 by the action of gravity. In the alternative, chamber 23 is equipped with clips or slots [not shown] which receive the support member 5. Or, in the further alternative, bottom surface 50 of the support member 5 has an adhesive strip [not shown] to allow the device 1 to be affixed to the wall 24.

The upwardly projecting edges 8*a* and 8*b* further serve to collect falling aerosol.

When in position in the chamber 23, support member 5 is oriented so that the lug 6 is adjacent to the door 30, thereby providing a handle to assist its removal when door 30 is opened.

Returning to FIG. 2, when the support member 5 is in a first position, the deflector 2 receives the aerosol 12 in its entrance 3, thereby preventing many of the droplets from contacting the wall 24 and other components inside the chamber 23. As explained, source performance may be compromised, if involatile salts and previously run samples accumulate on these surfaces.

In the embodiment illustrated in FIG. 2, the defector 2 has a passage 53 having a tube axis 40. The deflector 2 is attached to support member 5 so that when the device 1 is located in the chamber 23, the tube axis 40 is approximately aligned with the aerosol axis 13. This disposition ensures that the maximum quantity of material in the aerosol 12 enters the passage 53. Further, the tube axis 40 is not perpendicular to the support member 5, because the aerosol axis 13 is not perpendicular to the sampling axis 18 in the source illustrated in FIG. 2. Conveniently, the sampling axis 18 is parallel to the plane of the lower face of the wall 24 to facilitate construction of the chamber 23 and the evacuated chamber 19. However, it will be appreciated that the angle between the tube axis 40 and the support member 5 can be any value required to ensure approximate alignment of the tube axis 40 with the aerosol axis 13, whatever the value of the angle between the aerosol axis 13 and the sampling axis 18. It is noted that in many conventional sources, that angle is approximately 90°.

Charged particles travelling along the sampling axis 18 must pass unobstructed to the sampling housing 16 and inlet housing 17. To facilitate this, the entrance 3 of the deflector 2 comprises a cut-away portion 9 that is aligned with the sampling axis 18 when the device 1 is in its first position in the chamber 23. This allows unobstructed passage of the charged particles while maintaining the maximum reception of the aerosol in the entrance 3.

In another embodiment, illustrated in FIG. 4, the entrance 3 of the deflector 2 extends closer to the nebulizer 14 than it does in the FIG. 2 embodiment. An aperture 41 in the deflector 2 is therefore provided, aligned with the sampling axis 18.

FIG. 5 shows another embodiment in which the deflector 2 is shorter and terminates clear of the intersection of the aerosol axis 13 and the sampling axis 18. In this case there is no requirement for an aperture or cut-away portion in the deflector 2.

It will be appreciated that although the embodiments shown in FIGS. 1-5 comprise a deflector 2 in the form of a cylinder, this is by no means essential. Deflectors having, for example, elliptical, rectangular, square or any other polygonal cross sections could be used instead.

In the mass spectrometer and ionization source of FIG. 2, the exit 4 of the deflector 2 is located adjacent to an outlet port 39 in the lower face of the wall 24 when the device 1 is positioned in the chamber 23. This ensures that the material in the aerosol 12 that enters the deflector 2 through its entrance 3 is discharged through the outlet port 39 to a point outside the chamber. A discharge pipe (not shown) may be attached to the outlet port 39 to carry the discharged material to any suitable disposal point.

FIG. 6 shows another embodiment in which the deflector 2 comprises a concave shield 42. When in position in the chamber 23 the shield 42 extends only around a part of the aerosol 12, thereby avoiding obstruction of the sampling axis 18.

Other means for removably locating the deflector 2 in the chamber 23 may be used. For example, the means for removably locating may comprise a support member that engages in slots 43 (FIG. 3) in the wall 24, or projections or pegs may be provided on the wall 24 to support the plate member. In other embodiments, the means for removably locating may comprise a bracket 44 (FIG. 7) for locating a tubular deflector 45 comprising a bend. The exit 46 of such a deflector 45 may be cut as shown to align with the outlet port 39 in the wall not shown in FIG. 7 but assuming a position in a vertical wall. The bracket 44 may be located on the support member 5 in any suitable way, for example by welds, screws, dowels, lugs or slots. Such an arrangement may be suitable for use in ion sources whose orientation precludes the simple location by the action of gravity shown in FIG. 2.

A further embodiment of the present invention directed to a method of servicing an interface housing 23. Referring now to FIG. 2, the interface housing 10 has at least one wall 24 defining a chamber 23 and having at least one exit port 39 and at least one working port 55 in housing 17 in the wall 24. The chamber receives an aerosol having at least a working portion, an exiting portion and a falling portion. The working portion is received by the working port 55. The exiting portion flows past the working port 55 and is received by the exit port 39. And, the falling portion comprises a part of said aerosol that falls out of suspension in the chamber 23. The interface housing 10 further has a door means in the form of a door 30, for accessing the chamber, having an open position and a closed position. The method comprising the step of placing the door means 30 in an open position and removing, if present a manifold 1, and inserting a manifold 1 having a deflector 2 and a support member 5. The deflector 2 has aerosol deflecting surfaces and, in a first position, the deflector 2 is positioned for directing an aerosol flowing past the working ports 55a and 55b to the exit port. In a second position, the deflector is removed from the chamber 23. The support member 5 is affixed to the deflector 2 and has mounting means for removably mounting the deflector in the first position. In the second position, the support member 5 and the deflector 2 are removed from the chamber 23 to allow removal of said fallen portion of aerosol deposited on the manifold 1 or discarded. And, the method comprises the step of removably mounting the now cleaned support member 5 with the deflector 2 or a new support member 5 and deflector 2 in the first position.

Thus, embodiments of the present invention have been described with respect to the preferred embodiments with the understanding that the invention is capable of modification and alteration. Therefore, the invention should not be limited to the precise details set forth herein but should comprise such subject matter set forth in the claims that follow and their equivalents.

What is claimed is:

1. A device, for placement in a chamber of an interface housing, said interface housing having at least one wall defining said chamber and having at least one exit port and at least one working port in said wall, said chamber for receiving an aerosol said aerosol having at least a working portion, an exiting portion and a falling portion, said working portion is received by said at least one of working port, said exiting portion flowing past said working port and received by said exit port and said falling portion comprising a portion of said aerosol that falls out of suspension, comprising:
   a. a deflector having aerosol deflecting surfaces and in a first position in which said deflector is positioned for directing an aerosol flowing past said working port to said exit port and a second position in which said deflector is removed from said chamber;
   b. a support member affixed to said deflector and having mounting means for removably mounting said deflector in said first position and in said second position said support member and said deflector removed from said chamber to allow removal of said fallen portion of aerosol deposited on said device.

2. The device of claim 1 wherein said support member has at least one planar section having a top surface, a bottom surface and at least one edge surface, said at least one edge surface and bottom surface removably mounting to said at least one wall with said deflector in said first position and said top surface collecting fallen aerosol, and in said second position said support member removed from said chamber to allow removal of fallen aerosol deposited on said top surface.

3. The device of claim 1 wherein said deflector is a tubular member having a passage, said passage having a passage inlet and a passage outlet, said passage outlet in fluid communication with said exit port and said passage inlet receiving said aerosol as said deflector assumes said first position.

4. The device of claim 3 wherein said tubular member has a cross sectional form of selected from the group consisting of a circle, ellipse, oval, and multisided forms.

5. The device of claim 3 wherein said tubular member has an opening to allow working aerosol to enter said working port.

6. The device of claim 3 wherein said tubular member has a projection extending over said working port.

7. The device of claim 1 wherein said deflector is movably affixed to said support member to allow said deflector to be assume at least two orientations within said chamber.

8. The device of claim 1 wherein said chamber has a bottom and said support member in said first position has said planar section adjacent said bottom to collect fallen aerosol.

9. The device of claim 8 wherein said at least one edge has a containment ridge to collect fallen aerosol.

10. The device of claim 1 further comprising handle means affixed to at least one of said deflector and support member to facilitate manually grasping said device.

11. The device of claim 1 wherein said support member is retained in said first position by gravity.

12. The device of claim 1 wherein said support member engages said wall of said chamber in said first position.

13. A device, for receiving aerosols, comprising:
   a. an interface housing, said interface housing having at least one wall defining a chamber and having at least one exit port and at least one working port in said wall, said chamber for receiving an aerosol said aerosol having at least a working portion, an exiting portion and a falling portion, said working portion is received by said at least one of working ports, said exiting portion flowing past said at least one working port and received by said at least one exit port and said fallen portion flowing comprising a part of said aerosol that falls out of suspension,
   b. at least one manifold, said at least one manifold having a deflector and a support member, each of said at least one manifold having a first position and a second position, in said first position said manifold is in said chamber and in said second position, said manifold is removed from said chamber, said deflector having aerosol deflecting surfaces and in said first position said deflector is positioned for directing an aerosol flowing past said working port to said exit port and; said support member affixed to said deflector and having mounting means for removably mounting said deflector in said first position and in said second position said support member and said deflector removed from said chamber to allow removal of said fallen portion of aerosol deposited on said device.

14. The device of claim 13 wherein said interface housing is constructed and arranged to receive sequentially a plurality of manifolds.

15. The device of claim 14 wherein said manifold is disposable.

16. The device of claim 13 wherein said support member has at least one planar section having a top surface, a bottom surface and at least one edge surface, at least one of said edge surface and bottom surface removably mounting to said at least one wall with said deflector in said first position and said top surface collecting fallen aerosol, and in said second position said support member removed from said chamber to allow removal of fallen aerosol deposited on said top surface.

17. The device of claim 13 wherein said deflector is a tubular member having a passage, said passage having a passage inlet and a passage outlet, said passage outlet in fluid communication with said exit port and said passage inlet receiving said aerosol as said deflector assumes said first position.

18. The device of claim 13 wherein said tubular member has a cross sectional form selected from the group consisting of a circle, ellipse, oval, and multisided forms.

19. The device of claim 13 wherein said defector is movably affixed to said support member to allow said deflector to assume at least two orientations within said chamber.

20. The device of claim 13 wherein said chamber has a bottom and said support member in said first position has said planar section adjacent said bottom to collect fallen aerosol.

21. The device of claim 16 wherein said at least one edge has a containment ridge to collect fallen aerosol.

22. The device of claim 13 further comprising handle means affixed to at least one of said deflector and support member to facilitate manually grasping said device.

23. The device of claim 13 wherein said tubular member has an opening to allow working aerosol to enter said working port.

24. The device of claim 13 wherein said tubular member has a projection extending over said working port.

25. The device of claim 13 wherein said support member engages said wall of said chamber in said first position.

26. The device of claim 13 further comprising an ionization source selected from the group consisting of photoionization means, chemical ionization means and electrospray ionization means.

27. The device of claim 13 further comprising a at least one of the components of a mass spectrometer in communication with the working port, said components selected from the group consisting of linear quadrupole mass filters, quadrupole, cylindrical or linear ion traps, magnetic sector mass analysers, "Kingdon" trap mass analysers, ICR or Fourier Transform mass analysers, and time of flight mass analysers.

28. A method of servicing an interface housing, said interface housing having at least one wall defining said chamber and having at least one exit port and at least one working port in said wall, said chamber for receiving an aerosol said aerosol having at least a working portion, an exiting portion and a falling portion, said working portion is received by at least one of said working port, said exiting portion flowing past said working port and received by said exit port and said fallen portion flowing comprising a part of said aerosol that falls out of suspension, said interface housing having a door means having an open position and a closed position, said method comprising the step of:

placing said door means in an open position and removing, if present a manifold, and inserting a manifold having a defector and a support member, said deflector having aerosol deflecting surfaces and in a first position in which said deflector is positioned for directing an aerosol flowing past said working port to said exit port and a second position in which said deflector is removed from said chamber; said support member affixed to said deflector and having mounting means for removably mounting said deflector in said first position and in said second position said support member and said deflector removed from said chamber to allow removal of said fallen portion of aerosol deposited on said device;

removably mounting said support member with said deflector in said first position.

29. The method of claim 28 further comprising at least one of the steps consisting of cleaning the removed manifold and disposing said manifold.

\* \* \* \* \*